United States Patent

Arotin et al.

[11] Patent Number: 5,354,944
[45] Date of Patent: Oct. 11, 1994

[54] 4-CARBOXY-2-ARYLOXYPHENOXYALKYL SUBSTITUTED HETEROCYCLES USEFUL AS HERBICIDAL AGENTS

[75] Inventors: Robert L. Arotin, Yardley, Pa.; Michael A. Guaciaro, Hightstown, N.J.

[73] Assignee: American Cyanamid Company, Wayne, N.J.

[21] Appl. No.: 7,940

[22] Filed: Jan. 25, 1993

Related U.S. Application Data

[62] Division of Ser. No. 800,794, Nov. 27, 1991, Pat. No. 5,213,606.

[51] Int. Cl.5 .................... A01N 43/54; C07D 239/24
[52] U.S. Cl. ..................................... 504/136; 544/316; 544/318
[58] Field of Search .................. 549/316, 318; 504/136

[56] References Cited

U.S. PATENT DOCUMENTS

| | | | |
|---|---|---|---|
| 4,225,336 | 9/1980 | Fory et al. | 504/130 |
| 4,518,416 | 5/1985 | Forster et al. | 504/130 |
| 4,576,631 | 3/1986 | Carter | 504/130 |
| 4,750,931 | 6/1988 | Rogers | 504/136 |
| 4,943,584 | 7/1990 | Theobald et al. | 514/380 |

OTHER PUBLICATIONS

K. Hwang and S. K. Park, Synthetic Communications, 20, pp. 949–954 (1990).

Primary Examiner—C. Warren Ivy
Assistant Examiner—Zinna N. Davis
Attorney, Agent, or Firm—J. W. Hogan, Jr.

[57] ABSTRACT

4-Carboxy-2-aryloxyphenoxyalkyl substituted heterocycle compounds which are effective for the selective control of grass weed species in the presence of crops are described. Also described are a method for the selective herbicidal use of the compounds and methods for their preparation.

8 Claims, No Drawings

4-CARBOXY-2-ARYLOXYPHENOXYALKYL SUBSTITUTED HETEROCYCLES USEFUL AS HERBICIDAL AGENTS

This is a divisional of co-pending application Ser. No. 07/800,794 filed on Nov. 27, 1991, now U.S. Pat. No. 5,213,606.

BACKGROUND OF THE INVENTION

Grass weeds cause tremendous global economic losses by reducing crop yields and lowering crop values. In particular, blackgrass, barnyardgrass, ryegrass, green foxtail and wild oats cause extensive economic losses worldwide.

U.S. Pat. No. 4,225,336 discloses phenoxyalkyloxazolines which are useful as selective herbicides in cereals. U.S. Pat. No. 4,576,631 discloses certain aryloxyphenoxy oxoimidazolidines and U.S. Pat. No. 4,943,584 is directed to certain (p-Phenoxyphenoxy)-methyl-five-membered heteroaromatic compounds and their use for combatting pests. However, there remains an ongoing search in the art to create more effective and more selective herbicidal agents for the selective control of grass weeds growing in the presence of crops.

Both U.S. Pat. No. 4,750,931, which discloses herbicidal 3,5-disubstituted-2-pyridyloxy-fluorophenoxy-alkanoic acids and derivatives thereof, and U.S. Pat. No. 4,518,416, which discloses substituted pyridyl-phenyl ethers, are directed to compounds which are distinct from the compounds of the present invention.

K. Hwang and S. K. Park, Synthetic Communications, 20, pages 949–954 (1990) describe the synthesis of phenyl pyridyl ethers utilizing fluoride ion. However, the scope of the reaction is limited and high reaction temperatures are required.

It is, therefore, an object of the present invention to provide highly effective herbicidal agents useful for the selective control of grass weed species in the presence of crops.

SUMMARY OF THE INVENTION

The present invention relates to 4-carboxy-2-aryloxyphenoxyalkyl substituted heterocycles which are useful for the selective control of undesirable grass weed species in the presence of crops.

The 4-carboxy-2-aryloxyphenoxyalkyl substituted heterocycles of the present invention are illustrated as structural formula I:

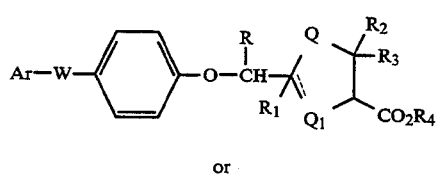

or

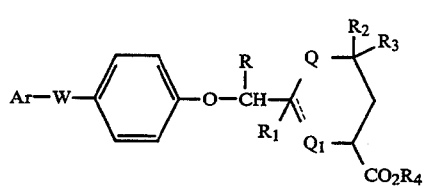

wherein Ar is selected from

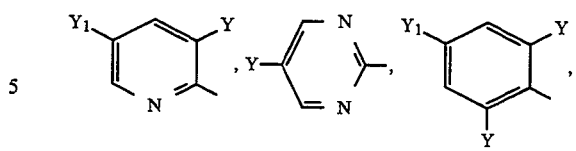

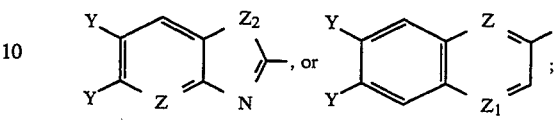

Y is hydrogen, halogen, nitro, cyano or $C_1$–$C_4$ haloalkyl;
$Y_1$ is halogen, nitro, cyano, $C_1$–$C_4$ haloalkyl or $C_1$–$C_4$ haloalkoxy;
W is O or S;
Z is N or CH;
$Z_1$ is N or $N^+$—$O^-$;
$Z_2$ is O or S;
R is $C_1$–$C_4$ alkyl;
═ indicates a single or double bond; $R_1$ and $R_2$ are each independently hydrogen or $C_1$–$C_4$ alkyl, with the proviso that when ═ indicates a double bond, then $R_1$ is not present;
$R_3$ is hydrogen, $C_1$–$C_4$ alkyl or $CO_2R_5$;
Q and $Q_1$ are each independently O, $S(O)_m$ or $NR_6$, with the proviso that when -- indicates a double bond then $Q_1$ is $NR_6$ and $R_6$ is not present;
m is an integer of 0, 1 or 2;
$R_6$ is hydrogen or $C_1$–$C_4$ alkyl;
$R_4$ and $R_5$ are each independently hydrogen,
  $C_1$–$C_4$ alkyl optionally substituted with halogen, $C_1$–$C_4$ alkoxy, furyl, phenyl, halophenyl, $C_1$–$C_4$ alkylphenyl or $C_1$–$C_4$ alkoxyphenyl,
  $C_3$–$C_6$ alkenyl optionally substituted with $C_1$–$C_4$ alkoxy, halogen or phenyl,
  $C_3$–$C_6$ alkynyl optionally substituted with halogen or
  an alkali metal, alkaline earth metal, manganese, copper, zinc, cobalt, silver, nickel, ammonium or organic ammonium cation;
the acid addition salts thereof when $R_6$ is hydrogen; and all optical isomers and diastereomers thereof.

The compounds of the present invention demonstrate selectivity on important agronomic crops such as wheat, barley, rice and soybean while effectively controlling numerous grass weed species such as blackgrass, barnyardgrass, green foxtail, wild oats, large crabgrass and ryegrass.

DETAILED DESCRIPTION OF THE INVENTION

Preferred formula I compounds of the present invention which are especially useful for the selective control of grass weed species in the presence of crops are those in which
Ar is selected from

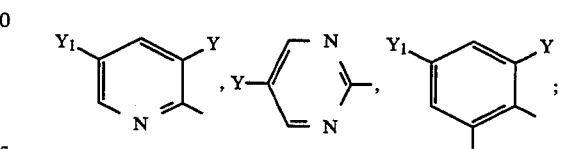

Y is hydrogen, halogen or $C_1$–$C_4$ haloalkyl;
$Y_1$ is halogen, $C_1$–$C_4$ haloalkyl or $C_1$–$C_4$ haloalkoxy;

W is O;

R is $C_1-C_4$ alkyl;

⸺ indicates a single or double bond;

$R_1$ and $R_2$ are each independently hydrogen or $C_1-C_4$ alkyl, with the proviso that when ⸺ indicates a double bond, then $R_1$ is not present;

$R_3$ is hydrogen, $C_1-C_4$ alkyl or $CO_2R_5$;

Q and $Q_1$ are each independently O, $S(O)_m$ or $NR_6$, with the proviso that when ⸺ indicates a double bond then $Q_1$ is $NR_6$, and $R_6$ is not present;

m is an integer of 0, 1 or 2;

$R_6$ is hydrogen or $C_1-C_4$ alkyl;

$R_4$ and $R_5$ are each independently hydrogen, $C_1-C_4$ alkyl optionally substituted with halogen, $C_1-C_4$ alkoxy, furyl, phenyl, halophenyl, $C_1-C_4$ alkylphenyl or $C_1-C_4$ alkoxyphenyl, $C_3-C_6$ alkenyl optionally substituted with $C_1-C_4$ alkoxy, halogen or phenyl, $C_3-C_6$ alkynyl optionally substituted with halogen or an alkali metal, alkaline earth metal, manganese, copper, zinc, cobalt, silver, nickel, ammonium or organic ammonium cation.

More preferred formula I compounds of the invention which are especially useful for the selective control of grass weed species such as blackgrass, large crabgrass, ryegrass, barnyardgrass and green foxtail in the presence of rice soybean and cereal crops such as wheat and barley have the following structural formula

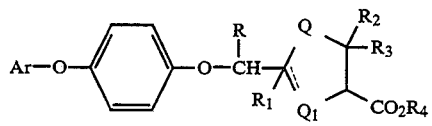

wherein Ar is selected from

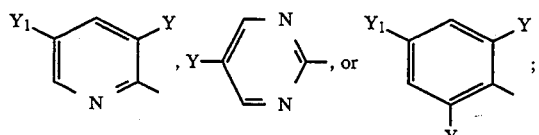

Y is hydrogen or halogen;

$Y_1$ is halogen, $C_1-C_4$ haloalkyl or $C_1-C_4$ haloalkoxy;

R is $C_1-C_4$ alkyl;

⸺ indicates a single or double bond;

$R_1$ and $R_2$ are each independently hydrogen or $C_1-C_4$ alkyl, with the proviso that when ⸺ indicates a double bond, then $R_1$ is not present;

$R_3$ is hydrogen, $C_1-C_4$ alkyl or $CO_2R_5$;

Q and $Q_1$ are each independently O, S or $NR_6$, with the proviso that when ⸺ indicates a double bond then $Q_1$ is $NR_6$ and $R_6$ is not present;

$R_6$ is hydrogen or $C_1-C_4$ alkyl; and $R_4$ and $R_5$ are each independently hydrogen, $C_1-C_4$ alkyl or an alkali metal, organic ammonium or ammonium cation.

In formula I above, alkali metals include: sodium, potassium and lithium, but sodium is generally preferred. Further, the term "organic ammonium" is defined as a group consisting of a positively charged nitrogen atom joined to from one to four aliphatic groups, each containing from one to sixteen carbon atoms. Exemplary of halogen hereinabove are fluorine, chlorine, bromine and iodine. The term "haloalkyl" is defined as a compound of the following formula $C_pH_qX_r$ where X is halogen and p, q and r are integers such that $q+r=2p+1$. The term "haloalkoxy" is defined as a compound of the following formula $C_pH_qX_rO$ where X is halogen and p, q and r are integers such that $q+r=2p+1$.

Certain formula I 4-carboxy-2-aryloxyphenoxyalkyl substituted heterocycles may be prepared by reacting a haloaryl compound of formula II with a dialkali metal salt of hydroquinone in the presence of an organic solvent such as dimethyl sulfoxide to yield the formula III p-(aryloxy)phenol. The p-(aryloxy)phenol is then reacted with a base such as potassium carbonate and a $C_1-C_4$ alkyl 2-halo-2-($C_1-C_4$ alkyl)acetate in the presence of an organic solvent such as dimethylformamide or acetonitrile, at an elevated temperature, to give the $C_1-C_4$ alkyl 2-[p-(aryloxyphenoxy)]-2-($C_1-C_4$ alkyl)acetate of formula IV. Reaction of the thus formed acetate with a reducing agent such as diisobutylaluminum hydride in the presence of an inert organic solvent such as toluene, at a reduced temperature, gives the formula V 2-[p-(aryloxyphenoxy)]-2-($C_1-C_4$ alkyl)acetaldehyde. Reaction of this acetaldehyde with a compound of formula VI and a base such as potassium acetate or triethylamine in the presence of an organic solvent, water or mixture thereof yields the formula I 4-carboxy-2-aryloxyphenoxyalkyl substituted heterocycle. This reaction scheme is illustrated in Flow Diagram I:

FLOW DIAGRAM I

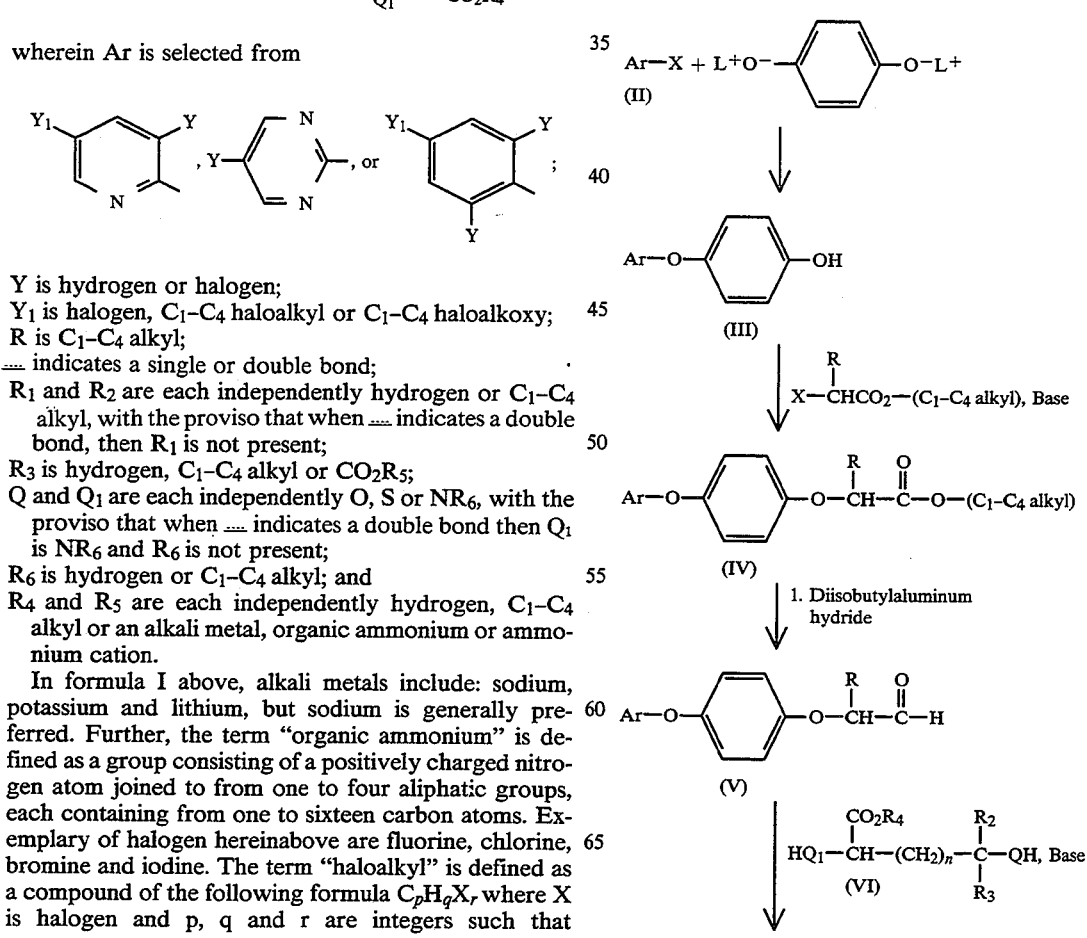

-continued
FLOW DIAGRAM I

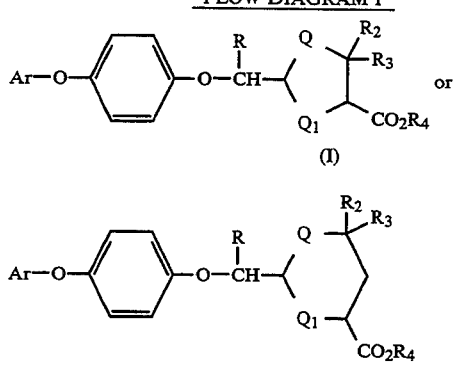

wherein Ar, R, Q, $Q_1$, $R_2$, and $R_3$ are as described above for formula I; n is an integer of 0 or 1; $R_4$ and $R_5$ are each independently hydrogen, $C_1$–$C_4$ alkyl optionally substituted with halogen, $C_1$–$C_4$ alkoxy, furyl, phenyl, halophenyl, $C_1$–$C_4$ alkylphenyl or $C_1$–$C_4$ alkoxyphenyl, $C_3$–$C_6$ alkenyl optionally substituted with $C_1$–$C_4$ alkoxy, halogen or phenyl, or $C_3$–$C_6$ alkynyl optionally substituted with halogen; X is Cl or Br and L is sodium or potassium.

Alternatively, certain formula I compounds wherein ═ indicates a double bond may be prepared by reacting a formula IV $C_1$–$C_4$ alkyl 2-[p-aryloxyphenoxy)]-2-($C_1$–$C_4$ alkyl)acetate compound with a base such as sodium hydroxide in the presence of a solvent to yield the 2-[p-(aryloxyphenoxy)]-2-($C_1$–$C_4$ alkyl)acetic acid of formula VII. The formula VII acetic acid is then reacted with thionyl chloride in the presence of an organic solvent such as chloroform, preferably at an elevated temperature, to give the acid chloride of formula VIII. Reaction of the thus formed acid chloride with a compound of formula IX and a base such as triethylamine in the presence of an organic solvent such as chloroform, preferably at a reduced temperature, gives the formula X 2-[p-(aryloxyphenoxy)]-2-($C_1$–$C_4$ alkyl)acetic acid amide. The formula X compound is then heated at reflux with azeotropic removal of water in the presence of an organic solvent such as benzene and p-toluenesulfonic acid to yield the formula I 4-carboxy-2-aryloxyphenoxyalkyl substituted heterocycle. This reaction scheme is illustrated in Flow Diagram II:

FLOW DIAGRAM II

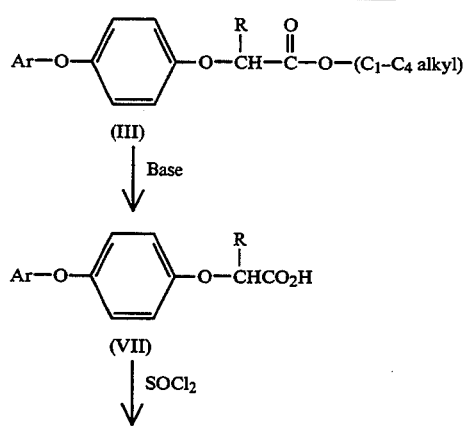

-continued
FLOW DIAGRAM II

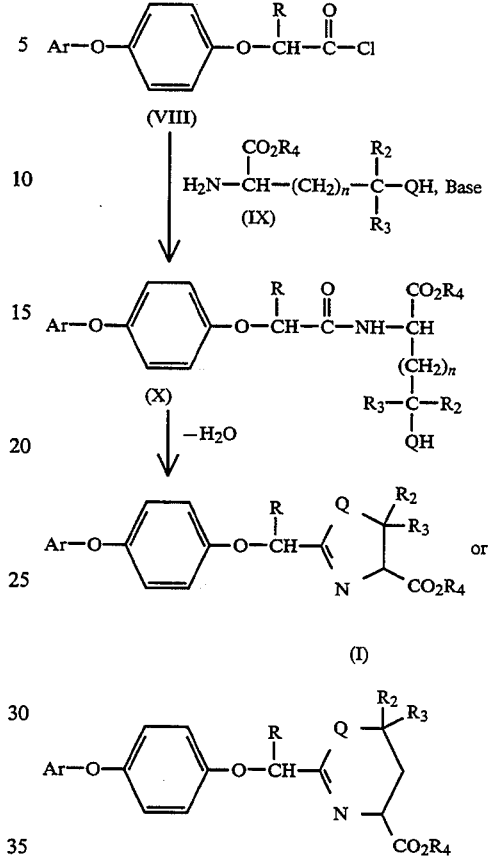

wherein Ar, R, Q, $R_2$, and $R_3$ are as described above for formula I; n is an integer of 0 or 1; and $R_4$ and $R_5$ are each independently hydrogen, $C_1$–$C_4$ alkyl optionally substituted with halogen, $C_1$–$C_4$ alkoxy, furyl, phenyl, halophenyl, $C_1$–$C_4$ alkylphenyl or $C_1$–$C_4$ alkoxyphenyl, $C_3$–$C_6$ alkenyl optionally substituted with $C_1$–$C_4$ alkoxy, halogen or phenyl, or $C_3$–$C_6$ alkynyl optionally substituted with halogen.

Advantageously, certain formula I 4-carboxy-2-aryloxyphenoxyalkyl substituted heterocycles may be prepared by reacting 4-benzyloxyphenol with a base such as potassium carbonate and a $C_1$–$C_4$ alkyl 2-halo-2-($C_1$–$C_4$ alkyl)acetate in the presence of an organic solvent such as 2-butanone, preferably at an elevated temperature, to give the $C_1$–$C_4$ alkyl 2-[p-(benzyloxy)phenoxy]-2-($C_1$–$C_4$ alkyl)acetate of formula XI. Reaction of the thus formed formula XI acetate with a reducing agent such as diisobutylaluminum hydride in the presence of an inert organic solvent such as toluene, at a reduced temperature, gives the formula XII 2-[p-(benzyloxy)phenoxy]-2-($C_1$–$C_4$ alkyl)acetaldehyde. The acetaldehyde is then deprotected under hydrogenation conditions using a catalyst such as palladium on carbon in the presence of an inert organic solvent such as ethanol to yield the 2-[p-hydroxyphenoxy]-2-($C_1$–$C_4$ alkyl)acetaldehyde of formula XIII. Reaction of the formula XIII acetaldehyde with a compound of formula VI and a base such as potassium acetate in the presence of a solvent gives the formula XIV 4-carboxy-2-(p-hydroxyphenoxy)alkyl substituted heterocycle. The substituted heterocycle is then reacted with potassium fluoride, which is on an inert support such as alumina or diatomaceous earth, and a haloaryl compound of formula II in the presence of an inert organic solvent such as acetonitrile, preferably at a temperature of from about 30° to 95° C., to give the formula I 4-carboxy-2-aryloxyphenoxyalkyl substituted heterocycle. This reaction scheme is illustrated below in Flow Diagram III:

phenyl, $C_1$-$C_4$ alkylphenyl or $C_1$-$C_4$ alkoxy phenyl; and X is Cl or Br.

Similarly, other formula I compounds wherein $R_1$ is $C_1$-$C_4$ alkyl may be prepared by the following reactions:

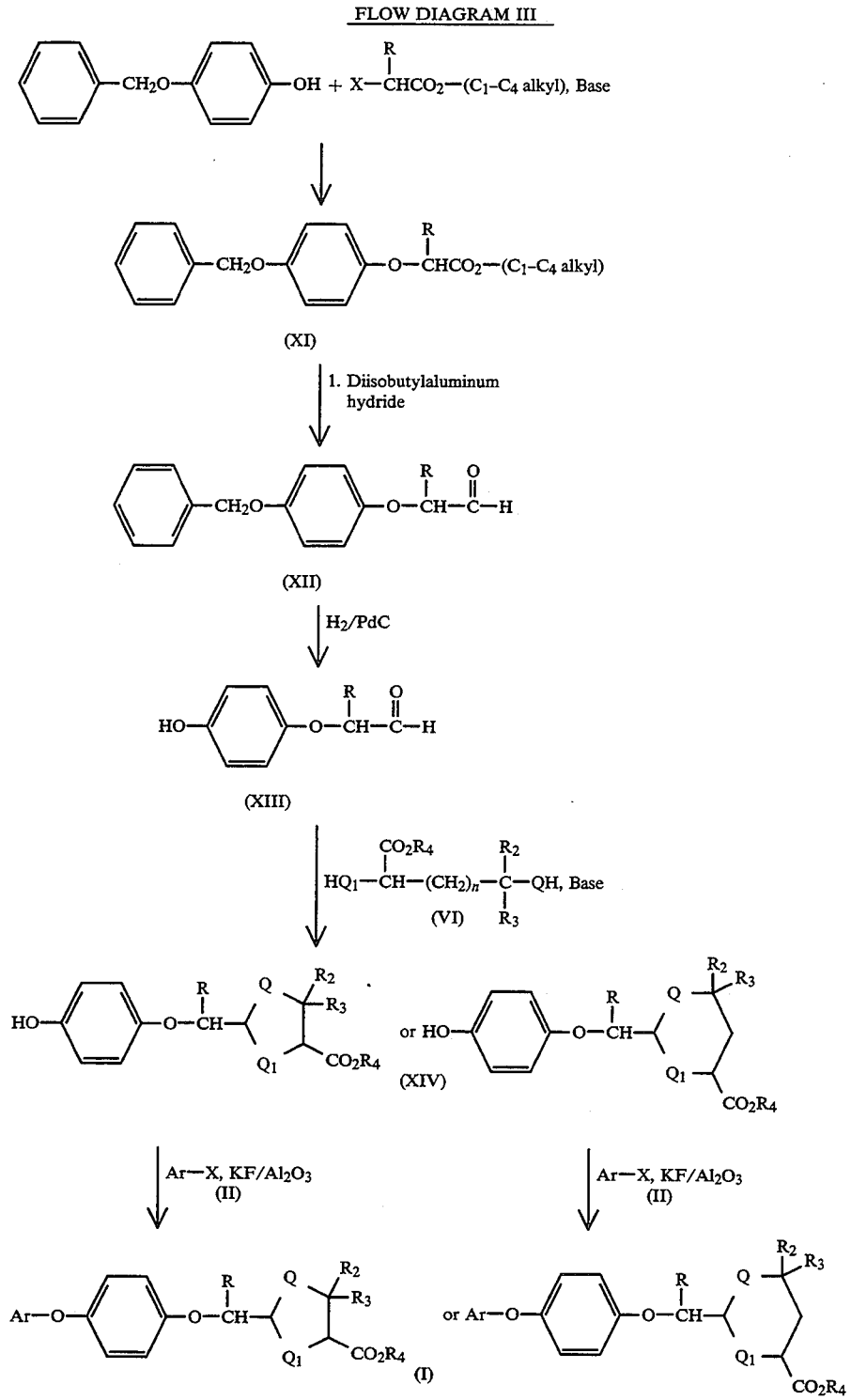

wherein Ar, R, Q, $Q_1$, $R_2$, and $R_3$ are as described above for formula I; n is an integer of 0 or 1; $R_4$ and $R_5$ are each independently hydrogen or $C_1$-$C_4$ alkyl optionally substituted with $C_1$-$C_4$ alkoxy, furyl, phenyl, halo-

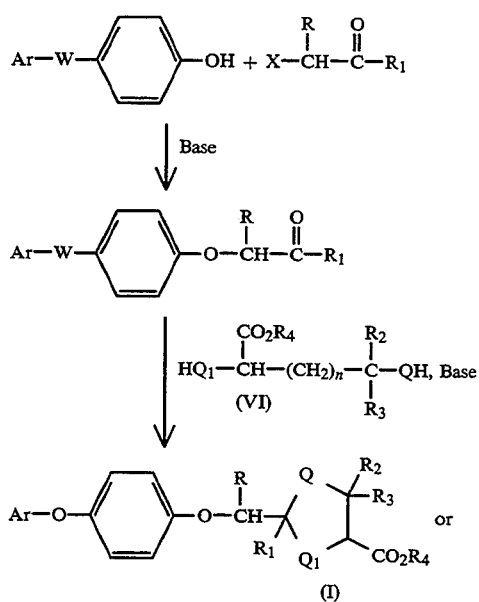

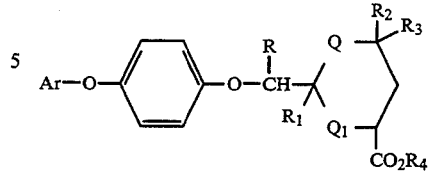

wherein Ar, W, R, $R_2$, and $R_3$ are as described above for formula I; n is an integer of 0 or 1; $R_1$ is $C_1$–$C_4$ alkyl; $R_4$ and $R_5$ are each independently hydrogen, $C_1$–$C_4$ alkyl optionally substituted with halogen, $C_1$–$C_4$ alkoxy, furyl, phenyl, halophenyl, $C_1$–$C_4$ alkylphenyl or $C_1$–$C_4$ alkoxyphenyl, $C_3$–$C_6$ alkenyl optionally substituted with $C_1$–$C_4$ alkoxy, halogen or phenyl, or $C_3$–$C_6$ alkynyl optionally substituted with halogen; and X is Cl or Br.

Another method of preparing certain formula I compounds wherein W is S is the following:

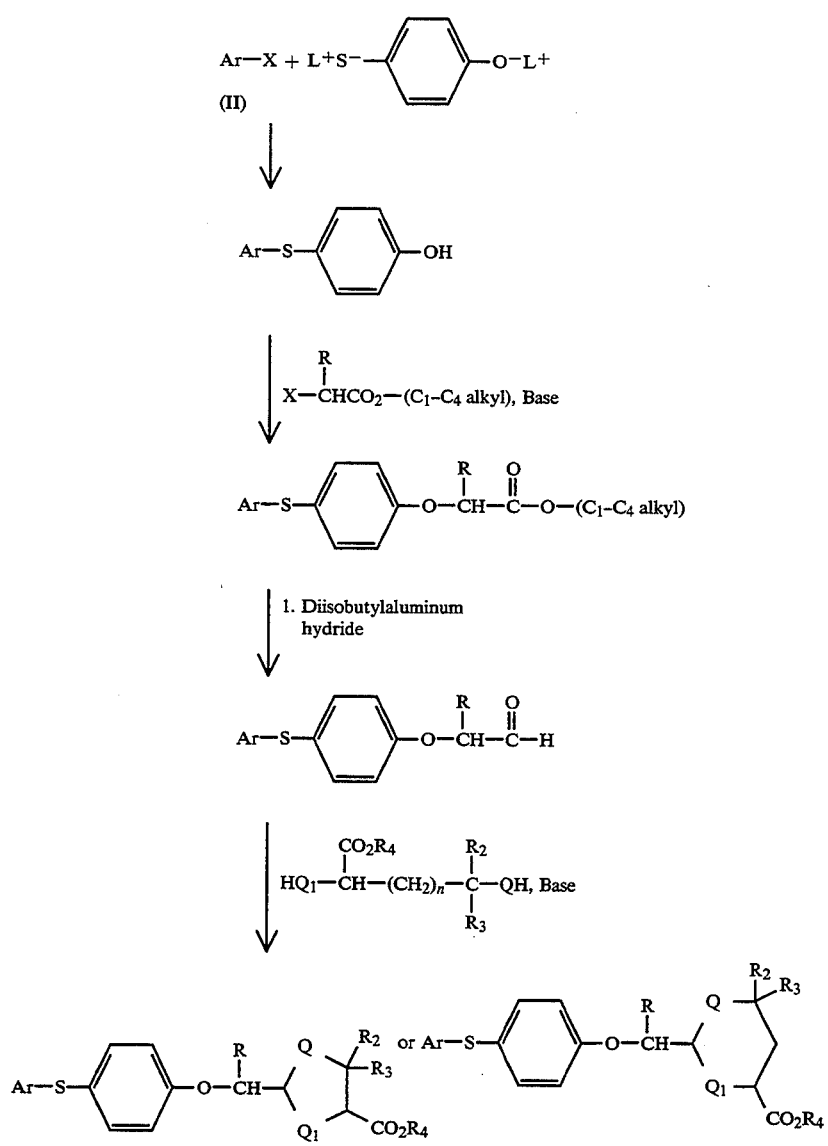

wherein Ar, R, Q, $Q_1$, $R_2$, and $R_3$ are as described above for formula I; n is an integer of 0 or 1; $R_4$ and $R_5$ are each independently hydrogen, $C_1$-$C_4$ alkyl optionally substituted with halogen, $C_1$-$C_4$ alkoxy, furyl, phenyl, halophenyl, $C_1$-$C_4$ alkylphenyl or $C_1$-$C_4$ alkoxyphenyl, $C_3$-$C_6$ alkenyl optionally substituted with $C_1$-$C_4$ alkoxy, halogen or phenyl, or $C_3$-$C_6$ alkynyl optionally substituted with halogen; X is Cl or Br and L is sodium or potassium.

Certain formula I compounds wherein W is S and ≡ indicates a double bond may be prepared by the following reactions:

oxy, halogen or phenyl, or $C_3$-$C_6$ alkynyl optionally substituted with halogen.

Advantageously, formula I compounds wherein $R_4$ and $R_5$ are each an alkali metal, alkaline earth metal, manganese, copper, zinc, cobalt, silver, nickel, ammonium or organic ammonium cation may be prepared from formula I compounds wherein $R_4$ and $R_5$ are hydrogen by conventional processes known to those skilled in the art.

Certain starting p-(aryloxy)phenol compounds of formula III may be prepared by reacting a haloaryl compound of formula II with 4-benzyloxyphenol and a

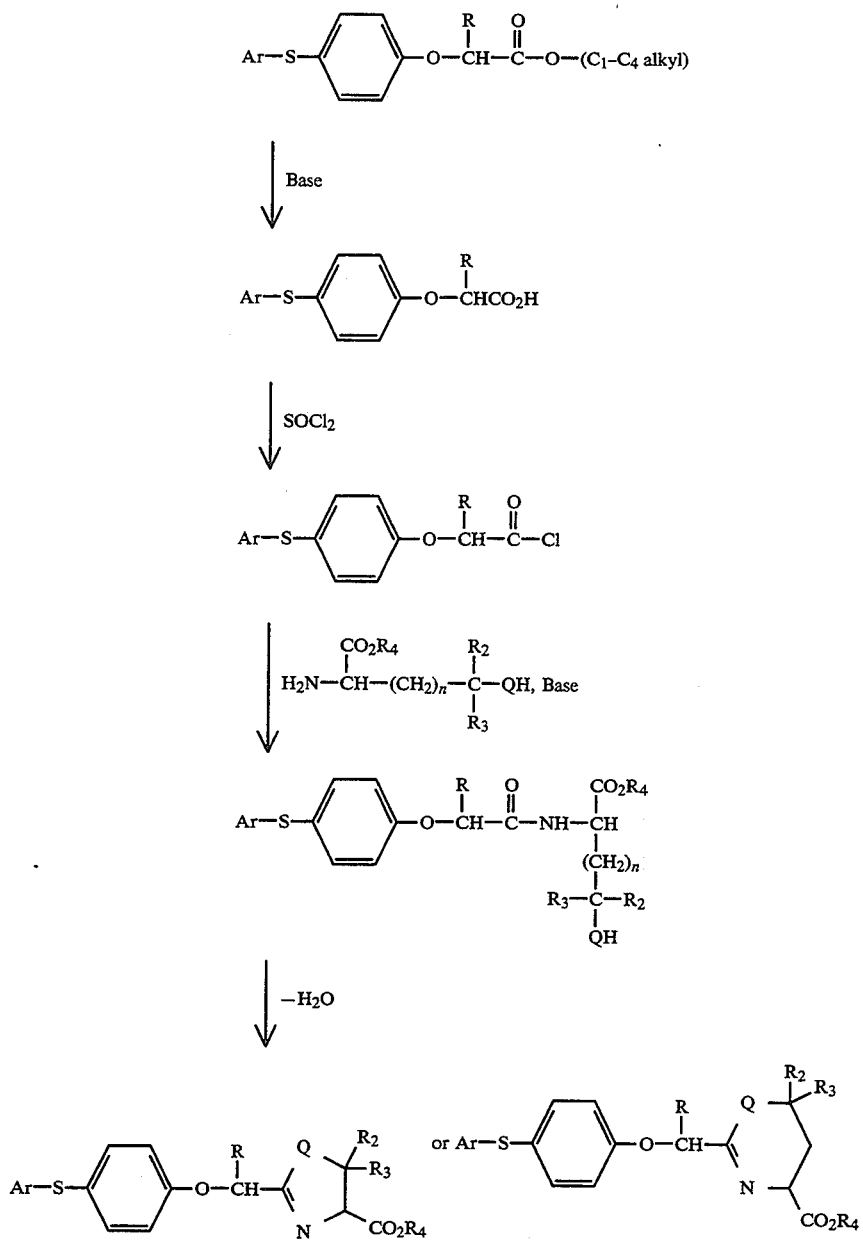

wherein Ar, R, Q, $R_2$, and $R_3$ are as described above for formula I; n is an integer of 0 or 1; and $R_4$ and $R_5$ are each independently hydrogen, $C_1$-$C_4$ alkyl optionally substituted with halogen, $C_1$-$C_4$ alkoxy, furyl, phenyl, halophenyl, $C_1$-$C_4$ alkylphenyl or $C_1$-$C_4$ alkoxyphenyl, $C_3$-$C_6$ alkenyl optionally substituted with $C_1$-$C_4$ alkbase such as potassium carbonate in the presence of an organic solvent such as dimethylformamide, at an elevated temperature, to yield the formula XV 2-[p-(benzyloxy)phenoxy]aryl compound. The formula XV compound is then reacted with hydrogen bromide in the presence of acetic acid to give the formula III p-(aryloxy)phenol. This reaction scheme is illustrated in Flow Diagram IV:

FLOW DIAGRAM IV

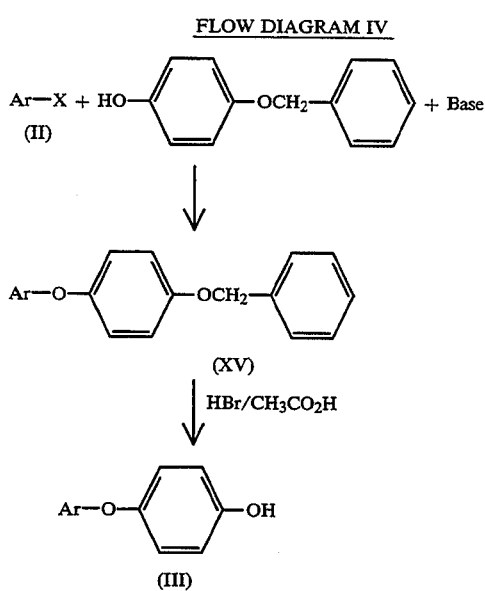

wherein Ar is as described above for formula I and X is Cl or Br.

Surprisingly, the 4-carboxy-2-aryloxyphenoxyalkyl substituted heterocycle compounds of the present invention demonstrate heightened selectivity on important agronomic crops such as wheat, barley, rice and soybean while effectively controlling numerous grass weed species.

The formula I compounds of the present invention are effective herbicidal agents useful for the selective control of grass weed species in the presence of cereal, rice and broadleaf crops. These compounds are effective for controlling grass weeds native to both dry land and wet land areas. The compounds are effective in controlling grass weeds when applied to the foliage thereof or to the soil or water containing seeds or other propagating organs of said weeds such as stolons, tubers or rhizomes, at rates of from about 0.016 to 1.0 kg/ha and preferably from about 0.032 to 0.8 kg/ha.

In practice, the formula I compounds may be applied to crops in the form of a solid or liquid herbicidal composition, comprising a herbicidally effective amount of the formula I compound dispersed or dissolved in an inert solid or liquid carrier. The formulations may be applied as preemerence or post-emergence treatments. The formulations may also be applied as foliar applications to the cereal crops after the grass weeds have emerged, rendering them eminently suitable for use in grass weed control in wheat and barley.

Advantageously, the formula I compounds can be formulated as emulsifiable concentrates, wettable powders, granular formulations, flowable concentrates and the like.

In order to facilitate a further understanding of the invention, the following examples are presented to illustrate more specific details thereof. The invention is not to be limited thereby except as defined in the claims.

EXAMPLE 1

Preparation of p-[(3,5-Dichloro-2-pyridyl)oxy]phenol

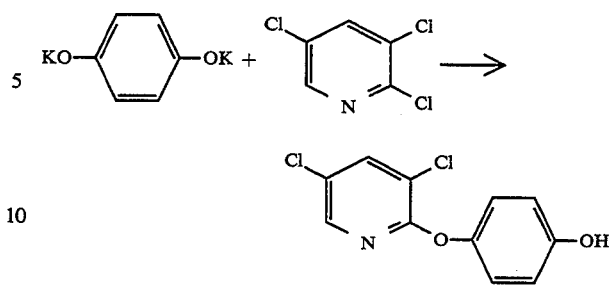

2,3,5-Trichloropyridine (69.32 g, 0.38 mol) and 18-crown-6 (4.0 g, 0.015 mol) are added to a mixture of the dipotassium salt of hydroquinone (prepared from hydroquinone (44.0 g, 0.4 mol) and potassium hydroxide (45.0 g, 0.8 mol)) in dimethyl sulfoxide (700 mL). The reaction mixture is stirred overnight at room temperature, heated at 60° C. for 2½ hours, diluted with water and extracted with ether. The combined organic extracts are washed with water, treated with charcoal, dried over anhydrous magnesium sulfate and concentrated in vacuo to obtain the title product as a white solid (47.23 g, mp 122°–123.5° C.).

EXAMPLE 2

Preparation of Ethyl 2-{p-[(3,5-dichloro-2-pyridyl)oxy]phenoxy}propionate

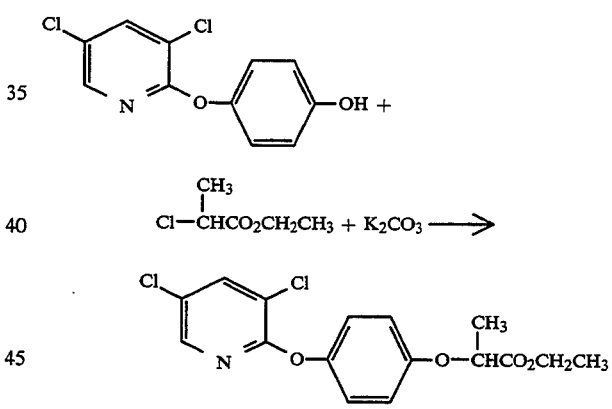

Potassium carbonate (867 g, 6.29 mol) is added to a mixture of p-[(3,5-dichloro-2-pyridyl)oxy]phenol (1,609 g, 6.29 mol), 18-crown-6 (50 g, 0.19 mol) and tetrabutylammonium hydrogen sulfate (50 g, 0.15 mol) in dimethylformamide (20 L). Ethyl 2-chloropropionate (1,380 g, 10.10 mol) is then added and the reaction mixture is stirred for 2 days at 85° C., diluted with water and extracted with methylene chloride. The combined organic extracts are washed sequentially with water, 2% sodium hydroxide solution and water and concentrated in vacuo to give a residue. The residue is dissolved into a 1:1 toluene/heptane solution, washed with 2% sodium hydroxide solution and concentrated in vacuo to obtain the title product as a dark red-brown liquid (1,445 g) which is identified by ¹H NMR spectral analysis.

EXAMPLE 3

Preparation of 2-{p-[(3,5-Dichloro-2-pyridyl)oxy]phenoxy}propionaldehyde

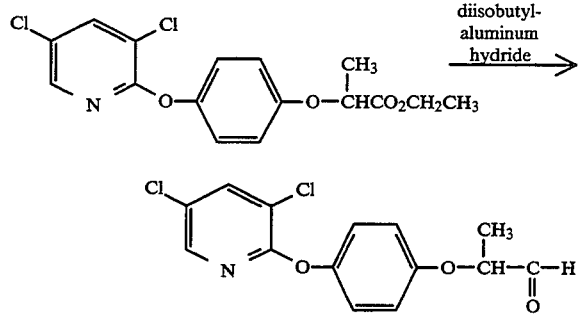

A solution of ethyl 2-{p-[(3,5-dichloro-2-pyridyl)oxy]phenoxy}propionate (1,455 g, 4.06 mol) in toluene (12 L) is cooled to −55° C. under a nitrogen atmosphere and diisobutylaluminum hydride (5.42 L of a 1.0M solution) is added over 2 hours. The reaction mixture is then stirred for 5 hours at −55° C. and glacial acetic acid (1.8 L) is added dropwise, while allowing the mixture to exotherm to 15° C. Heptane (12 L) is added and the mixture is washed sequentially with 5% hydrochloric acid solution, water, saturated sodium bicarbonate solution and water and concentrated in vacuo to obtain the title product as a yellow-orange liquid (1,159 g) which is identified by $^1$H NMR spectral analysis.

Following the above procedure, but substituting the appropriate propionate for ethyl 2-{p-[(3,5-dichloro-2-pyridyl)oxy]phenoxy}propionate yields the following compounds.

2-{p-{[3-Chloro-5-(trifluoromethyl)-2-pyridyl]oxy}phenoxy}propionaldehyde and

2-{p-[(2-chloro-a,a,a-trifluoro-p-tolyl)oxy]-phenoxy}propionaldehyde.

EXAMPLE 4

Preparation of Ethyl 2-{1-{p-[(3,5-dichloro-2-pyridyl)oxy]phenoxy}ethyl}-4R-thiazolidinecarboxylate, mixture of diastereomers

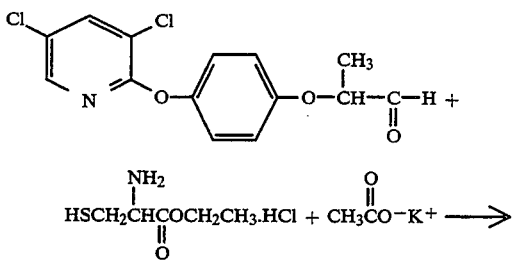

A solution of 2-{p-[(3,5-dichloro-2-pyridyl)oxy]phenoxy}propionaldehyde (50 g, 0.016 mol) in acetone (25 mL) is added dropwise to a mixture of L-cysteine ethyl ester hydrochloride (3.3 g, 0.0177 mol) and potassium acetate (1.75 g, 0.0177 mol) in 1:1 acetone/water (60 mL). The reaction mixture is stirred for 90 hours at room temperature. Next, 2 mL of water is added and the acetone is removed in vacuo to obtain an oil in water residue. The water is decanted from the oil and the oil is taken up in ether. The organic solution is washed with water, dried over anhydrous magnesium sulfate and evaporated in vacuo to obtain a light yellow viscous oil. Flash chromatography of the oil using silica gel and eluting with 60/40 methylene chloride/hexanes to 100% methylene chloride followed by 98/2 methylene chloride/ethyl acetate to 96/4 methylene chloride/ethyl acetate gives the title product as a light yellow viscous oil (4.9 g) which is identified by $^1$H NMR spectral analysis.

Following the above procedure, but utilizing the appropriate propionaldehyde and the appropriate cysteine or cysteine ester yields the following compounds:

2-{1-{p-[(3,5-Dichloro-2-pyridyl)oxy]phenoxy}ethyl}-4R-thiazolidinecarboxYlic acid, mixture of diastereomers, mp 94°–96° C.;

2-{1-{p-[(3,5-dichloro-2-pyridyl)oxy]phenoxy}ethyl}-4S-thiazolidinecarboxylic acid, mixture of diastereomers, colorless glass;

ethyl 2-{1-{p-[(2-chloro-a,a,a-trifluoro-p-tolyl)oxy]phenoxy}ethyl}-4R-thiazolidinecarboxylate, mixture of diastereomers, colorless viscous oil;

ethyl 2-{1-{p-{[3-chloro-5-(trifluoromethyl)-2-pyridyl]oxy}phenoxy}ethyl}-4R-thiazolidinecarboxylate, mixture of diastereomers, viscous oil; and ethyl 2-{1-{p-[(5-bromo-2-pyrimidinyl)oxy]phenoxy}ethyl}-4R-thiazolidinecarboxylate, mixture of diastereomers, colorless syrup.

EXAMPLE 5

Preparation of Ethyl 2-{1-{p-[(3,5-dichloro-2-pyridyl)oxy]phenoxy}ethyl}-4R-thiazolidinecarboxylate hydrochloride and ethyl 2-{1-{p-[(3,5-dichloro-2-pyridyl)oxy]phenoxy}ethyl}-4R-thiazolidincarboxylate

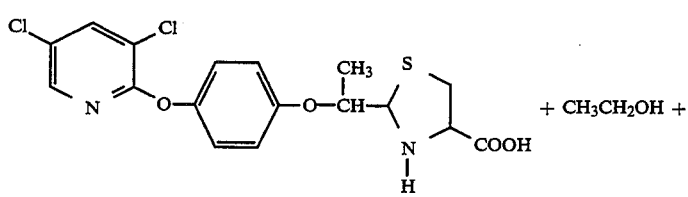

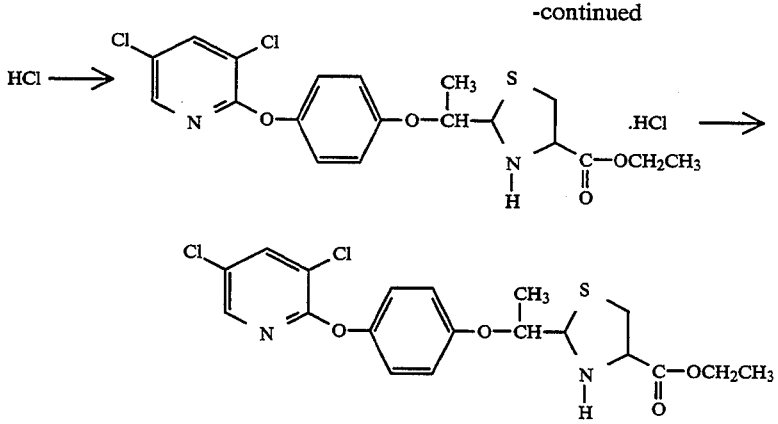

Hydrogen chloride gas is bubbled into a mixture of 2-{1-{p-[(3,5-dichloro-2-pyridyl)oxy]phenxoy}ethyl-4R-thiazolidinecarboxylic acid, mixture of diastereomers (5.0 g, 0.012 mol) in ethanol. The solid dissolves and the addition is continued while maintaining the reaction mixture temperature below 50° C. After the addition is complete, the reaction mixture is stirred at about 50° C. for 2 hours and concentrated in vacuo to give an oil. Ether is added to the oil and a solid forms. The solid is collected and washed with ether to obtain ethyl 2-{1-{p-[(3,5-dichloro-2-pyridyl)oxy] phenoxy}ethyl}-4R-thiazolidinecarboxylate hydrochloride as a white solid, mp 149°–153° C. Sodium hydrogen carbonate is then added to a mixture of the thus-formed salt in a 2:1 ether/water mixture until the aqueous phase remains basic. The organic phase is then separated, washed with water, dried over anhydrous magnesium sulfate and concentrated in vacuo to obtain a yellow oil. Flash chromatography of the oil using silica gel and eluting with 80/20 methylene chloride/hexanes to 100% methylene chloride followed by 1% to 5% ethyl acetate in methylene chloride gives ethyl 2-{1-{p-[(3,5-dichloro-2-pyridyl)oxy]phenoxy}ethyl}-4R-thiazolidinecarboxylate as a colorless oil.

Microanalysis for ethyl 2-{-1-{p-[(3,5-dichloro-2-pyridyl)oxy]phenoxy}ethyl}-4R-thiazolidinecarboxylate C19H20Cl2N2O4S Calcd: C, 51.47%; H, 4.54%; N, 6.31%; S, 7.23; Cl, 15.99% Found: C, 51.39%; H, 4.50%; N, 6.27%; S, 7.26%; Cl, 15.82%

Following the above procedure, but substituting methanol for ethanol yields methyl 2-{1-{p-[(3,5-dichloro-2-pyridyl)oxy]phenoxy}ethyl}-4R-thiazolidinecarboxylate as a colorless oil.

Microanalysis C18H18Cl2N2O4S

Calcd: C, 50.35%; H, 4.22%; N, 6.52%; S, 7.46%; Cl, 16.51% Found: C, 50.47%; H, 4.28%; N, 6.47%; S, 7.37%; Cl, 16.57%

EXAMPLE 6

Preparation of 2-{p-[(3,5-Dichloro-2-pyridyl)oxy]phenoxy}propionic acid

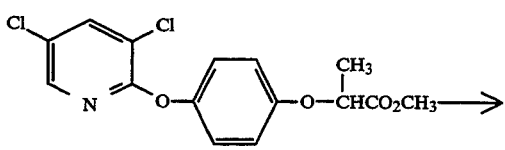

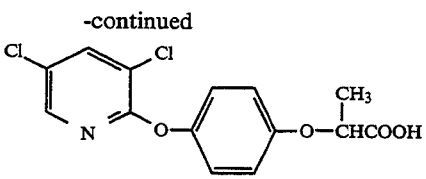

10% Sodium hydroxide solution (170 mL, 0.424 mol) is added to a solution of ethyl 2-{p-[(3,5-dichloro-2-pyridyl)oxy]phenoxy}propionate (79.09 g, 0.212 mol) in tetrahydrofuran with stirring. The reaction mixture is heated to 52° C., stirred for 3 hours, concentrated in vacuo and diluted with water. The aqueous solution is washed with methylene chloride, acidified with concentrated sulfuric acid and extracted with ethyl acetate. The combined organic extracts are dried and concentrated in vacuo to give the title product as a white solid (48.7 g) which is identified by $^1$H NMR spectral analysis.

EXAMPLE 7

Preparation of 2-{p-[(3,5-dichloro-2-pyridyl)oxy]phenoxy}propionyl chloride

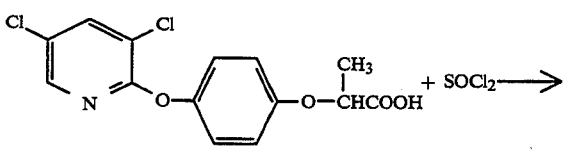

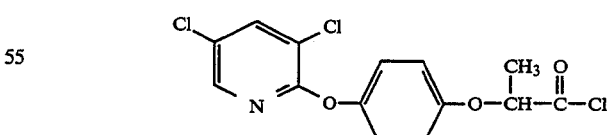

Thionyl chloride (18.8 mL, 257.1 mmol) is added dropwise to a mixture of 2-{p-[(3,5-dichloro-2-pyridyl)oxy]phenoxy}propionic acid (21.1 g, 64.3 mmol) in chloroform (220 mL). When the addition is complete, dimethylformamide (1.5 mL) is added and the reaction mixture is stirred for 21 hours at 63° C., concentrated in vacuo and chased with chloroform to obtain the title product as a yellow syrup which is identified by $^1$H NMR spectral analysis.

EXAMPLE 8

Preparation of Ethyl N-{2-{p-[(3,5-dichloro-2-pyridyl)-oxy]phenoxy}propionyl]cysteine, L-

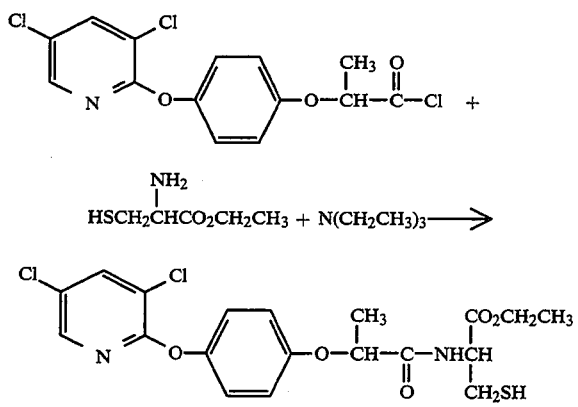

Triethylamine is added to a stirred mixture of L-cysteine ethyl ester hydrochloride (2.71 g, 14.66 mmol) in chloroform under nitrogen. After the reaction mixture is cooled to 0° C., a solution of 2-{p-[(3,5-dichloro-2-pyridyl)oxy]phenoxy}propionyl chloride (5.08 g, 14.66 mmol) in chloroform (30 mL) is added dropwise with stirring. The reaction mixture is then stirred overnight at room temperature, concentrated in vacuo and filtered to obtain a semi-solid. Chromatography of the semi-solid using silica gel and eluting with methylene chloride followed by 2% to 5% ethyl acetate in methylene chloride gives the title product as a white solid, mp 89°–91° C.

EXAMPLE 9

Preparation of Ethyl 2-{1-{p-[(3,5-dichloro-2-pyridyl)oxy]phenoxy}ethyl}-2-thiazoline-4R-carboxylate, [R,R and S,R], [S,R or R,R] and [R,R or S,R]

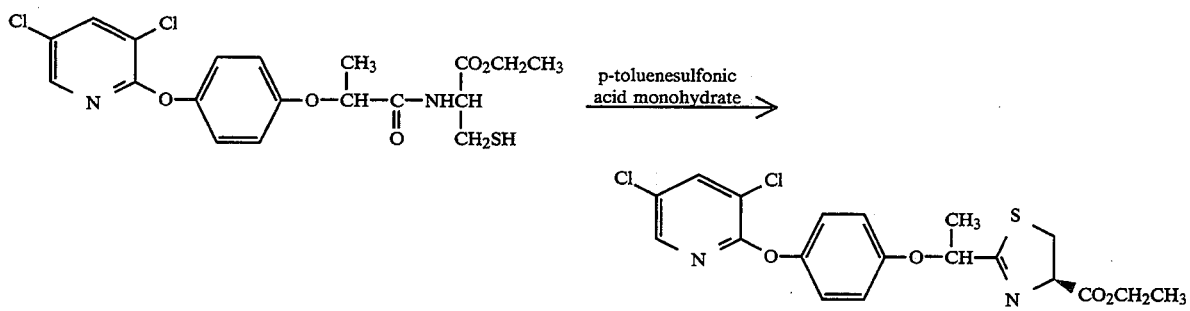

A solution of p-toluenesulfonic acid monohydrate (1.43 g, 7.54 mmol) in benzene is heated at reflux with azeotropic removal of water for 1 hour. Next, ethyl N-{2-{p-[(3,5-dichloro-2-pyridyl)oxy]phenoxy}propionyl}cysteine, L- (3.15 g, 6.86 mmol) is added and the reaction mixture is heated at reflux with azeotropic removal of water for 4 hours, stirred at room temperature overnight, heated at reflux for 2 hours, cooled to room temperature and diluted with water. The organic phase is separated, washed with water and brine, dried and concentrated in vacuo to obtain a yellow syrup. Flash chromatography of the syrup using silica gel and eluting with 10% to 15% ethyl acetate in methylene chloride gives the following products:

Ethyl 2-{1-{p-[(3,5-dichloro-2-pyridyl)oxy]phenoxy}ethyl}-2-thiazoline-4R-carboxylate, [R,R or S,R), 0.49 g;

ethyl 2-{1-{p-[(3,5-dichloro-2-pyridyl)oxy]-phenoxy}ethyl}-2-thiazoline-4R-carboxylate, [R,R and S,R], 0.58 g; and ethyl 2-{1-{p-[(3,5-dichloro-2-pyridyl)oxy]phenoxy}ethyl)-2-thiazoline-4R-carboxylate, [S,R or R,R], 0.29 g; which are identified by $^1$H NMR spectral analyses.

EXAMPLE 10

Preparation of 2-[p-(Benzyloxy)phenoxy]-3-chloro-5-(trifluoromethyl)pyridine

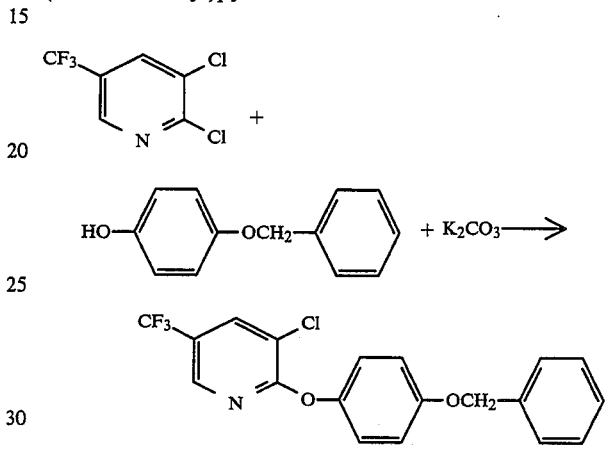

A mixture of 2,3-dichloro-5-trifluoromethylpyridine (33.3 g, 0.154 mol), 4-(benzyloxy)phenol (30.0 g, 0.15 mol) and potassium carbonate (21.5 g, 0.154 mol) in dimethylformamide (250 mL) is stirred for 2½ hours at about 90°–96° C. The reaction mixture is then cooled, stirred overnight at room temperature and concentrated in vacuo to obtain a residue. The residue is poured into water and a yellow solid forms. The solid is collected, washed with water, air dried and dissolved in ether. The organic solution is washed with water, treated with charcoal, dried over anhydrous magnesium sulfate and concentrated in vacuo to give the title product as a white solid (56 g, mp 82.5°–83.5° C.).

EXAMPLE 11

Preparation of p-{[3-Chloro-5-(trifluoromethyl)-2-pyridyl]oxy}phenol

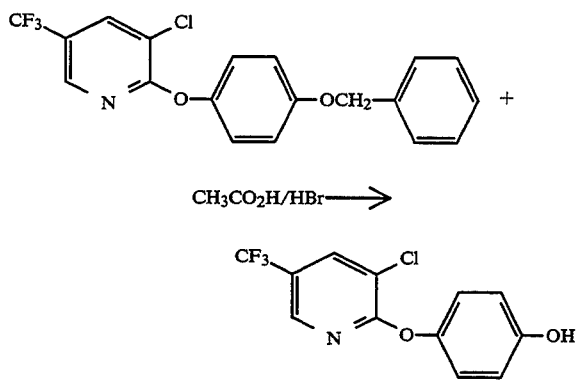

CH₃CO₂H/HBr ⟶

2-[p-(Benzyloxy)phenoxy]-3-chloro-5-(trifluoromethyl)pyridine (2.0 g, 0.00526 mol) is added to a 30% hydrogen bromide/acetic acid solution. The reaction mixture is stirred overnight at room temperature, poured into water and extracted with ether. The combined organic extracts are washed sequentially with water and saturated sodium hydrogen carbonate solution, dried over anhydrous magnesium sulfate and evaporated in vacuo to obtain a yellow oil. The oil is dissolved in an ether/hexanes solution and insoluble solids are removed by filtration through celite. The filtrate is concentrated in vacuo and the residue is passed through a short silica gel column eluting with 80/20 to 90/10 methylene chloride/ethyl acetate to obtain the title product as a colorless glass (1.1 g, mp 127°–129° C.).

EXAMPLE 12

Preparation of Methyl 2-[p-(benzyloxy)phenoxy]propionate

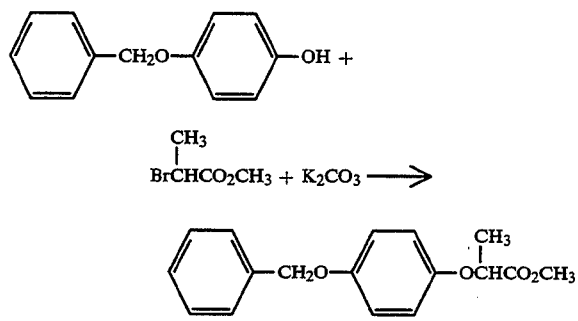

A mixture of 4-(benzyloxy)phenol (60.1 g, 0.30 mol), methyl 2-bromopropionate (50.1 g, 0.30 mol) and potassium carbonate (45.61 g, 0.33 mol) in 2-butanone is heated at reflux for 24 hours. TLC shows that starting material is present. Additional potassium carbonate (10 g, 0.07 mol) and methyl 2-bromopropionate (10 g, 0.06 mol) are added and the reaction mixture is heated at reflux overnight and filtered.

The filtrate is concentrated in vacuo to obtain a residue which contains starting material. The residue is dissolved in acetonitrile then potassium carbonate (25 g, 0.18 mol) and methyl 2-bromopropionate (30 g, 0.18 mol) are added and the reaction mixture is heated at reflux for 4 hours and filtered. The filtrate is concentrated in vacuo to obtain an oil. The oil is then washed with hexanes to obtain the title product as a white solid (58.8 g, mp 66°–68° C.).

EXAMPLE 13

Preparation of 2-[p-(Benxyloxy)phenoxy]propionaldehyde

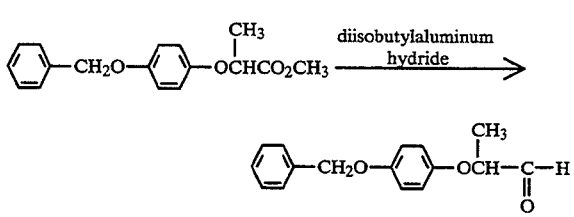

A 1.5 molar solution of diisobutylaluminum hydride in toluene (138 mL, 0.207 mol) is added dropwise to a mixture of methyl 2-[p-(benzyloxy)phenoxy]propionate (56.4 g, 0.197 mol) in toluene at −65° C. under a nitrogen atmosphere. The reaction mixture is stirred at −65° C. for 5 hours. Acetic acid (70 mL) is added dropwise and the reaction mixture is warmed to room temperature, diluted with hexanes, washed with 10% hydrochloric acid solution and water, dried and concentrated in vacuo to obtain an oil. Flash chromatography of the oil using silica gel and eluting with a 1:1 methylene chloride/hexanes solution gives the title product as a white solid (21.44 g, mp 50°–51° C.).

EXAMPLE 14

Preparation of 2-(p-Hydroxyphenoxy)propionaldehyde

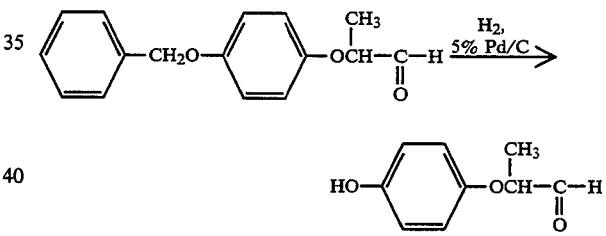

A mixture of 2-[p-(benzyloxy)phenoxy]propionaldehyde (34.6 g, 0.135 mol) and 5% Pd on carbon (2.0 g) in ethanol (250 mL) is placed on a Parr hydrogenator. Over 5 hours, the pressure drops from 37 psi to 28 psi. The reaction mixture is then filtered through celite and concentrated in vacuo to obtain a dark yellow syrup. Flash chromatography of the syrup using silica gel and eluting with methylene chloride followed by 1% to 10% ethyl acetate in methylene chloride gives the title product as a dark yellow syrup (8.2 g) which is identified by ¹H NMR spectral analysis.

EXAMPLE 15

Preparation of Ethyl 2-[1-(p-hydroxyphenoxy)ethyl]-4R-thiazolidinecarboxylate, mixture of diastereomers

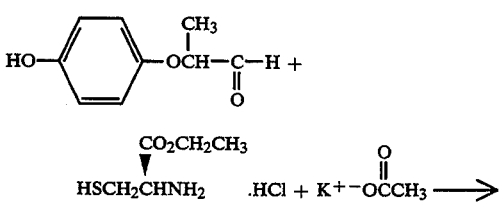

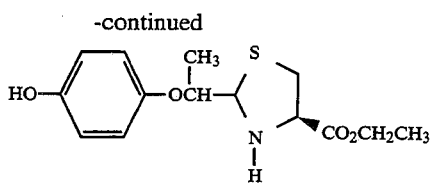

A solution of 2-(p-hydroxyphenoxy)propionaldehyde (4.7 g, 28.28 mmol) in acetone (75 mL) is added to a solution of L-cysteine ethyl ester hydrochloride (5.78 g, 31.10 mmol) and potassium acetate (3.05 g, 31.11 mmol) in a 1:1 acetone/water solution (80 mL). When the addition is complete, water (30 mL) is added and the reaction mixture is stirred overnight at room temperature and concentrated in vacuo to obtain a residue which is extracted with methylene chloride. The combined organic extracts are dried and concentrated in vacuo to obtain a solid. Flash chromatography of the solid using silica gel and eluting with methylene chloride followed by 5% to 15% ethyl acetate in methylene chloride gives the title product as a white solid (4.34 g, mp 99°–100° C.).

EXAMPLE 16

Preparation of Ethyl 2-{1-{p- [3-chloro-5-(trifluoromethyl)-2-pyridyl]oxy}phenoxy}ethyl}-4R-thiazolidinecarboxylate, mixture of diastereomers

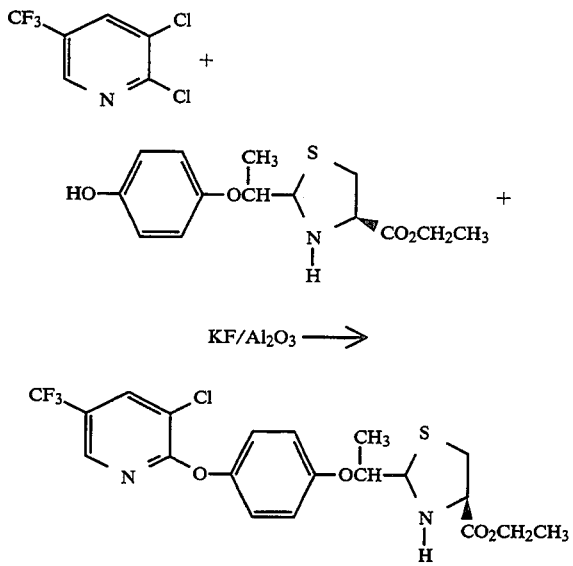

A mixture of 2,3-dichloro-5-trifluoromethylpyridine (0.809 g, 3.77 mmol), ethyl 2-[1-(p-hydroxyphenoxy)ethyl]-4R-thiazolidinecarboxYlate, mixture of diastereomers (1.12 g, 3.77 mmol) and potassium fluoride on alumina (40% KF, 2.19 g, 15.08 mmol) in acetonitrile (25 mL) is stirred for 18 hours at 72° C., 8 hours at 82° C., 2 days at room temperature and 8 hours at 82° C. under a nitrogen atmosphere. The reaction mixture is then filtered and concentrated in vacuo to obtain a brown syrup. Flash chromatography of the syrup using silica gel and eluting with 0% to 2% ethyl acetate in methylene chloride gives the title product as a pale yellow syrup (1.16 g) which is identified by ¹H NMR spectral analysis.

EXAMPLE 17

Preparation of 2-{p-[(5-Bromo-2-pyrimidinyl)oxy]phenoxy}propionaldehyde

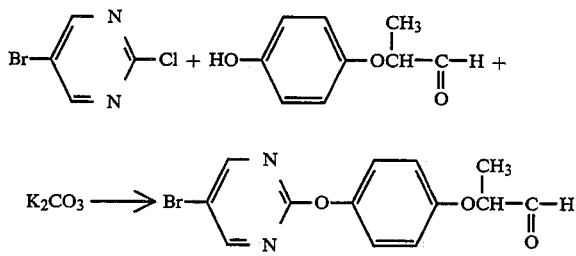

A mixture of 5-bromo-2-chloropyrimidine (4.54 g, 23.47 mmol), 2-(p-hydroxyphenoxy)propionaldehyde (3.90 g, 23.47 mmol) and potassium carbonate (4.05 g, 29.34 mmol) in acetonitrile is stirred for 18 hours at 70° C. under a nitrogen atmosphere. The reaction mixture is cooled to room temperature, filtered and the filter cake is washed with acetone and methylene chloride. The combined filtrates are concentrated in vacuo to obtain a brown semi-solid. Flash chromatography of the semi-solid using silica gel and eluting with methylene chloride gives the title product as a white solid (2.49 g, mp 97°–98° C.).

EXAMPLE 18

Preparation of Sodium 2-{p-[(3,5-dichloro-2-pyridyl)oxy]phenoxy}-1-hydroxy-1-propanesulfonate

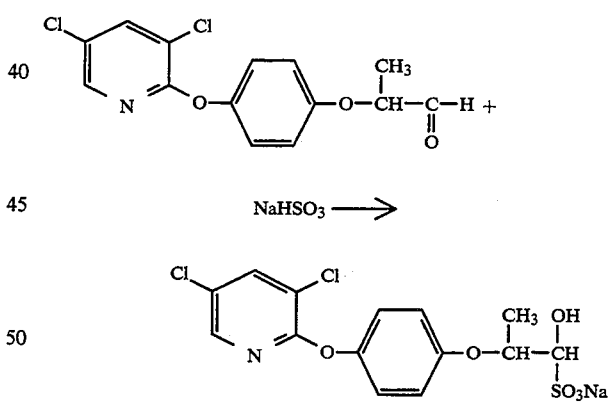

A solution of 2-{p-[(3,5-dichloro-2-pyridyl)oxy]phenoxy}propionaldehyde (25.38 g, 0.0813 mol) in methanol (300 mL) is added dropwise to a solution of sodium bisulfite (10.2 g, 0.0976 mol) in water (100 mL). The reaction mixture is stirred for 4 days at room temperature and filtered. The filter cake is dried in a vacuum oven overnight to obtain the title product as a white solid (24.6 g, mp 172°–173° C.).

EXAMPLE 19

Preparation of Ethyl 2-{1-{p-[(3,5-dichloro-2-pyridyl)oxy]phenoxy}ethyl-4R-thiazolidinecarboxylate, mixture of diastereomers

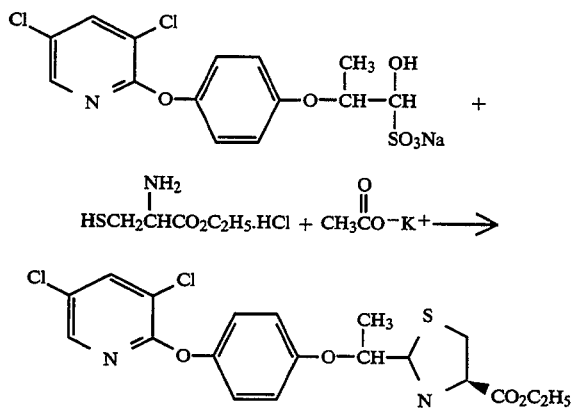

A mixture of sodium 2-{p-[(3,5-dichloro-2-pyridyl)oxy]phenoxy}-1-hydroxy-1-propanesulfonate (73.8 g, 0.177 mol), L-cysteine ethyl ester hydrochloride (36.2 g, 0.195 mol) and potassium acetate (19.2 g, 0.195 mol) in a 2.5/1 acetone/water solution is stirred overnight at room temperature, filtered through celite and concentrated in vacuo to obtain an oil in water mixture. Water is added and the mixture is extracted with ether. The combined organic extracts are washed sequentially with water, 20% sodium hydrogen carbonate solution, water and brine, treated with charcoal, dried over anhydrous magnesium sulfate and concentrated in vacuo to give the title product as a light yellow viscous oil (73.1 g) which is identified by $^1$H NMR spectral analysis.

EXAMPLE 20

Postemergence herbicidal evaluation of test compounds

The postemergence herbicidal activity of the compounds of the present invention is demonstrated by the following tests. Seedling plants are grown in jiffy flats for about two weeks. The test compounds are dispersed in 50/50 acetone/water mixtures containing 0.5% TWEEN, 20, a polyoxyethylene sorbitan monolaurate surfactant of Atlas Chemical Industries, in sufficient quantities to provide the equivalent of about 0.063 to 1.000 kilograms per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants are examined and rated according to the rating system set forth below. Data obtained are reported in Table I below. Where more than one test is involved for a given compound, the data are averaged.

Plant species employed in these evaluations are reported by header abbreviation, common name and scientific name.

Herbicide Rating Scale

Results of herbicide evaluation are expressed on a rating scale (0–9). The scale is based upon a visual observation of plant stand, vigor, malformation, size, chlorosis and overall appearance as compared with a control.

| Rating | Meaning | % Control Compared To Check |
|---|---|---|
| 9 | Complete kill | 100 |
| 8 | Approaching Complete kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |

| PLANT SPECIES EMPLOYED IN HERBICIDAL EVALUATIONS | | |
|---|---|---|
| HEADER ABB | COMMON NAME | SCIENTIFIC NAME |
| BARNYARDGR | BARNYARDGRASS | ECHINOCHLOA CRUS-GALLI, (L) BEAU |
| BLACKGRASS | BLACKGRASS | ALOPECURUS MYOSUROIDES |
| LARGE CRAB | CRABGRASS, (HAIRY) LARGE | DIGITARIA SANGUINALIS, (L) SCOP |
| GREEN FOX | FOXTAIL, GREEN | SETARIA VIRIDIS, (L) BEAUV |
| WILD OATS | OAT, WILD | AVENA FATUA, L. |
| RYE GRASS | RYEGRASS SP. | LOLIUM SP. |
| SOYBEAN WI | SOYBEAN WILLIAMS | GLYCINE MAX |
| S WHT KATE | WHEAT, SPRING CV. KATEPWA | TRITICUM AESTIVUM |
| BRLYBNZA | BARLEY, SPRING CV. BONANZA | HORDEUM VULGARE |
| RICE, TEBON | RICE CV. TEBONNET | ORYZA SATIVA |

TABLE I

POSTEMERGENCE TESTS

| Compound | Rate (kg/ha) | BARNY ARDGR | BLACK GRASS | LARGE CRAB | GREEN FOX | WILD OATS | RYE GRASS | SOYBE AN WI | S WHT KATE | BRLYB NZA | RICE, TEBON |
|---|---|---|---|---|---|---|---|---|---|---|---|
| Ethyl 2-{1-{p-[(3,5-dichloro-2-pyridyl)-oxy]phenoxy}ethyl}-4R-thiazolidinecarboxylate, mixture of diastereomers | 1.000 | 9.0 | 9.0 | 9.0 | 9.0 | 9.0 | 9.0 | 0.0 | 3.7 | 3.5 | 7.0 |
| | .500 | 9.0 | 9.0 | 9.0 | 9.0 | 7.9 | 7.7 | 0.0 | 1.0 | 3.7 | 4.9 |
| | .250 | 9.0 | 8.7 | 9.0 | 9.0 | 6.1 | 5.7 | 0.0 | 1.0 | 2.3 | 2.7 |
| | .125 | 9.0 | 7.7 | 9.0 | 9.0 | 4.6 | 3.4 | 0.0 | 0.6 | 0.6 | 1.9 |
| | .063 | 6.6 | 5.8 | 7.4 | 8.9 | 2.1 | 1.1 | 0.0 | 0.3 | 0.3 | 0.3 |
| Ethyl 2-{1-{p-[(5-bromo-2-pyrimidinyl)-oxy]phenoxy}ethyl}-4R-thiazolidine-carboxylate, mixture of diastereomers | 1.000 | 9.0 | 8.0 | 9.0 | 9.0 | 0.0 | 0.0 | 0.0 | 5.0 | 4.0 | 7.0 |
| | .500 | 9.0 | 5.0 | 3.0 | 9.0 | 0.0 | 0.0 | 0.0 | 4.0 | 4.0 | 4.0 |
| | .250 | 6.0 | 4.0 | 0.0 | 6.0 | 0.0 | 0.0 | 0.0 | 2.0 | 2.0 | 2.0 |
| Ethyl 2-{1-{p-[(2-chloro-alpha,alpha,-alpha-trifluoro-p- | 1.000 | 9.0 | 9.0 | 6.0 | 9.0 | 9.0 | 7.0 | 0.0 | 1.0 | 1.0 | 1.0 |
| | .500 | 8.0 | 8.0 | 5.0 | 9.0 | 0.0 | 3.0 | 0.0 | 0.0 | 0.0 | 0.0 |
| | .250 | 0.0 | 5.0 | 0.0 | 9.0 | 0.0 | 1.0 | 0.0 | 0.0 | 0.0 | 0.0 |

TABLE I-continued

POSTEMERGENCE TESTS

| Compound | Rate (kg/ha) | BARNY ARDGR | BLACK GRASS | LARGE CRAB | GREEN FOX | WILD OATS | RYE GRASS | SOYBE AN WI | S WHT KATE | BRLYB NZA | RICE, TEBON |
|---|---|---|---|---|---|---|---|---|---|---|---|
| tolyl)oxy]phenoxy}-ethyl}4R-thiazo-lidinecarboxylate, mixture of diastereomers | | | | | | | | | | | |
| 2-{1-{p-[(3,5-di-chloro-2-pyridyl)-oxy]phenoxy}ethyl}-4R-thiazolidine-carboxylic acid, mixture of diastereomers | .500 | 9.0 | 9.0 | 9.0 | 9.0 | 9.0 | 9.0 | 0.0 | 5.0 | 9.0 | 8.0 |
| | .250 | 9.0 | 9.0 | 9.0 | 9.0 | 9.0 | 7.0 | 0.0 | 3.0 | 6.0 | 8.0 |
| | .125 | 8.0 | 9.0 | 9.0 | 9.0 | 8.0 | 5.0 | 0.0 | 1.0 | 4.0 | 3.0 |
| | .063 | 9.0 | 9.0 | 9.0 | 9.0 | 9.0 | 0.0 | 0.0 | 1.0 | 1.0 | 0.0 |
| | .031 | 9.0 | 9.0 | 3.0 | 8.0 | 3.0 | 0.0 | 0.0 | 0.0 | 0.0 | 0.0 |
| Ethyl 2-{1-{p-[(3,5-dichloro-2-pyridyl)-oxy]phenoxy}ethyl}-2-thiazoline-4R-carboxylate, [R,R and S,R] | .500 | 9.0 | — | 8.0 | 9.0 | 5.0 | 3.0 | 0.0 | 0.0 | 3.0 | 2.0 |
| | .250 | 9.0 | — | 8.0 | 9.0 | 6.0 | 0.0 | 0.0 | 0.0 | 0.0 | 2.0 |
| | .125 | 7.0 | — | 3.0 | 8.0 | 3.0 | 0.0 | 0.0 | 0.0 | 0.0 | 0.0 |
| 2-{1-{p-[(3,5-dichloro-2-pyridyl)-oxy]phenoxy}ethyl}-4S-thiazolidine-carboxylic acid, mixture of diastereomers | .500 | 9.0 | 9.0 | 9.0 | 9.0 | 5.0 | 6.0 | 0.0 | 3.0 | 4.0 | 5.0 |
| | .250 | 9.0 | 9.0 | 9.0 | 9.0 | 5.0 | 5.0 | 0.0 | 0.0 | 2.0 | 0.0 |
| | .125 | 9.0 | 9.0 | 9.0 | 9.0 | 8.0 | 0.0 | 0.0 | 0.0 | 0.0 | 0.0 |
| | .063 | 9.0 | 5.0 | 7.0 | 9.0 | 5.0 | 0.0 | 0.0 | 0.0 | 0.0 | 0.0 |
| | .031 | 9.0 | 5.0 | 6.0 | 9.0 | 4.0 | 0.0 | 0.0 | 0.0 | 0.0 | 0.0 |
| | .016 | 9.0 | 6.0 | 3.0 | 8.0 | 0.0 | 0.0 | 0.0 | 0.0 | 0.0 | 0.0 |
| Ethyl 2-{1-{p-[(3,5-dichloro-2-pyridyl)-oxy]phenoxy}ethyl}-2-thiazoline-4R-carboxylate, [S,R or R,R] | .500 | 8.0 | 9.0 | 0.0 | 7.0 | 0.0 | 3.0 | 0.0 | 0.0 | 0.0 | 0.0 |
| | .250 | 7.0 | 7.0 | 6.0 | 8.0 | 0.0 | 0.0 | 0.0 | 0.0 | 0.0 | 0.0 |
| | .125 | 0.0 | 0.0 | 0.0 | 8.0 | 0.0 | 0.0 | 0.0 | 0.0 | 0.0 | 0.0 |
| Ethyl 2-{1-{p-[(3,5-dichloro-2-pyridyl)-oxy]phenoxy}ethyl}-2-thiazoline-4R-carboxylate, [R,R or S,R] | .500 | 9.0 | 9.0 | 9.0 | 9.0 | 0.0 | 9.0 | 0.0 | 0.0 | 2.0 | 0.0 |
| | .250 | 9.0 | 9.0 | 9.0 | 9.0 | 5.0 | 7.0 | 0.0 | 0.0 | 0.0 | 0.0 |
| | .125 | 9.0 | 5.0 | 4.0 | 8.0 | 0.0 | 4.0 | 0.0 | 0.0 | 0.0 | 0.0 |
| | .063 | 9.0 | 6.0 | 0.0 | 9.0 | 0.0 | 3.0 | 0.0 | 0.0 | 0.0 | 0.0 |
| | .031 | 6.0 | 0.0 | 0.0 | 9.0 | 0.0 | 0.0 | 0.0 | 0.0 | 0.0 | 0.0 |

EXAMPLE 21

Preemergence herbicidal evaluation of test compounds

The preemergence herbicidal activity of the compounds of the present invention is demonstrated by the following tests. Seeds or propagating organs of each plant species are separately mixed with potting soil and planted on top of approximately one inch of soil in separate pint cups. After planting, the cups are sprayed with the selected aqueous acetone solution containing test compound in sufficient quantity to provide the equivalent of about 0.125 to 1.000 kilograms per hectare of test compound per cup. The treated cups are then placed on greenhouse benches, watered and cared for in accordance with conventional greenhouse procedures. From four to five weeks after treatment, the tests are terminated and each cup is examined and rated according to the rating system provided in Example 20 above. The data obtained are recorded in Table II below.

TABLE II

PREMERGENCE TESTS

| Compound | Rate (kg/ha) | BARNY ARDGR | BLACK GRASS | LARGE CRAB | GREEN FOX | WILD OATS | RYE GRASS | SOYBE AN WI | S WHT KATE |
|---|---|---|---|---|---|---|---|---|---|
| Ethyl 2-{1-{p-((3,5-dichloro-2-pyridyl)-oxy]phenoxy}ethyl}-4R-thiazolidinecar-boxylate, mixture of diastereomers | 1.000 | 9.0 | 9.0 | 9.0 | 9.0 | 8.5 | 9.0 | 0.0 | 9.0 |
| | .500 | 9.0 | 9.0 | 9.0 | 9.0 | 8.0 | 9.0 | 0.0 | 8.0 |
| | .250 | 9.0 | 9.0 | 9.0 | 9.0 | 5.7 | 9.0 | 0.0 | 9.0 |
| | .125 | 9.0 | 9.0 | 9.0 | 9.0 | 3.0 | 9.0 | 0.0 | 6.0 |
| | .063 | 6.7 | 8.3 | 6.7 | 9.0 | 2.3 | 5.3 | 0.0 | 0.0 |
| Ethyl 2-{1-{p-[(5-bromo-2-pyrimidinyl)-oxy]phenoxy}ethyl}-4R-thiazolidine-carboxylate, mixture of diastereomers | .500 | 5.0 | 9.0 | 8.0 | 9.0 | 6.0 | 9.0 | 0.0 | 7.0 |
| | .250 | 5.0 | 7.0 | 5.0 | 9.0 | 2.0 | 7.0 | 0.0 | 0.0 |
| | .125 | 4.0 | 5.0 | 3.0 | 8.0 | 0.0 | 0.0 | 0.0 | 0.0 |
| Ethyl 2-{1-{p-[(2-chloro-alpha,alpha-alpha-trifluoro-p-tolyl)oxy]phenoxy}-ethyl}4R-thia-zolidinecarboxylate, mixture of diastereomers | 1.000 | 9.0 | 9.0 | 9.0 | 9.0 | 9.0 | 9.0 | 0.0 | 9.0 |
| | .500 | 9.0 | 9.0 | 9.0 | 9.0 | 7.0 | 9.0 | 0.0 | 9.0 |
| | .250 | 9.0 | 9.0 | 6.0 | 9.0 | 5.0 | 9.0 | 0.0 | 0.0 |
| | .125 | 9.0 | 9.0 | 3.0 | 9.0 | 0.0 | 9.0 | 0.0 | 0.0 |
| | .063 | 9.0 | 9.0 | 0.0 | 9.0 | 0.0 | 5.0 | 0.0 | 0.0 |
| | .031 | 9.0 | 9.0 | 0.0 | 0.0 | 0.0 | 4.0 | 0.0 | 0.0 |

TABLE II-continued

| Compound | Rate (kg/ha) | PREMERGENCE TESTS ||||||||
| --- | --- | --- | --- | --- | --- | --- | --- | --- | --- |
| | | BARNY ARDGR | BLACK GRASS | LARGE CRAB | GREEN FOX | WILD OATS | RYE GRASS | SOYBE AN WI | S WHT KATE |
| Ethyl 2-{1-{p-{[3-chloro-5-(trifluoro-methyl)-2-pyridyl]-oxy}phenoxy}ethyl}-4R-thiazolidine-carboxylate, mixture of diastereomers | 1.000 | 9.0 | 9.0 | 9.0 | 9.0 | 9.0 | 9.0 | 0.0 | 9.0 |
| | .500 | 9.0 | 9.0 | 9.0 | 9.0 | 9.0 | 9.0 | 0.0 | 9.0 |
| | .250 | 9.0 | 9.0 | 9.0 | 9.0 | 9.0 | 9.0 | 0.0 | 9.0 |
| | .125 | 9.0 | 9.0 | 9.0 | 9.0 | 9.0 | 9.0 | 0.0 | 9.0 |
| | .063 | 9.0 | 9.0 | 9.0 | 9.0 | 6.0 | 9.0 | 0.0 | 3.0 |
| | .031 | 6.0 | 9.0 | 5.0 | 9.0 | 2.0 | 8.0 | 0.0 | 0.0 |

We claim:

1. A compound having the structural formula

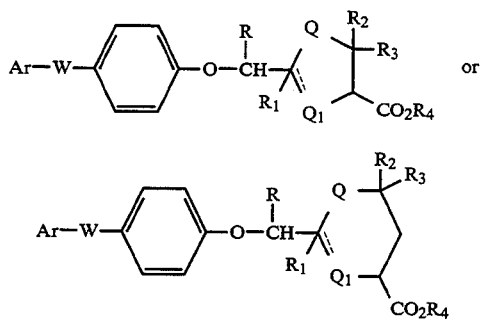 or wherein Ar is

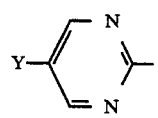

$Y$ is hydrogen, halogen, nitro, cyano or $C_1-C_4$ haloalkyl;
$W$ is O or S;
$R$ is $C_1-C_4$ alkyl;
$\rightleftharpoons$ indicates a single or double bond;
$R_1$ and $R_2$ are each independently hydrogen or $C_1-C_4$ alkyl, with the proviso that when $\rightleftharpoons$ indicates a double bond, then $R_1$ is not present;
$R_3$ is hydrogen, $C_1-C_4$ alkyl or $CO_2R_5$;
$Q$ is $S(O)_m$ and $Q_1$ is $NR_6$, with the proviso that when $\rightleftharpoons$ indicates a double bond then $R_6$ is not present;
$m$ is an integer of 0, 1 or 2;
$R_6$ is hydrogen or $C_1-C_4$ alkyl;
$R_4$ and $R_5$ are each independently hydrogen,
$C_1-C_4$ alkyl optionally substituted with halogen, $C_1-C_4$ alkoxy, furyl, phenyl, halophenyl, $C_1-C_4$alkylphenyl or $C_1-C_4$ alkoxyphenyl,
$C_3-C_6$ alkenyl optionally substituted with $C_1-C_4$alkoxy, halogen or phenyl,
$C_3-C_6$ alkynyl optionally substituted with halogen, or an alkali metal, alkaline earth metal, manganese, copper, zinc, cobalt, silver, nickel, ammonium or organic ammonium cation;

the acid addition salts thereof when $R_6$ is hydrogen; or optical isomers or diastereomers thereof.

2. The compound according to claim 1 wherein $Y$ is hydrogen, halogen or $C_1-C_4$ haloalkyl; and $W$ is O.

3. The compound according to claim 2 having the structure

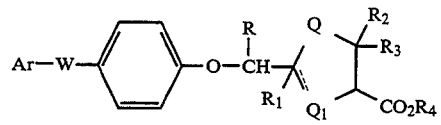

wherein
$Y$ is hydrogen or halogen;
$m$ is O; and
$R_4$ and $R_5$ are each independently hydrogen, $C_1-C_4$ alkyl or an alkali metal, organic ammonium or ammonium cation.

4. A method for controlling undesirable grass weed species which comprises applying to the foliage or stems of the desirable vegetation or to the soil or water containing seeds or other propagating organs of the undesirable vegetation a herbicidally effective amount of a compound having the structure

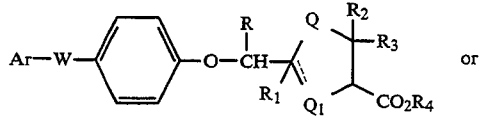 or

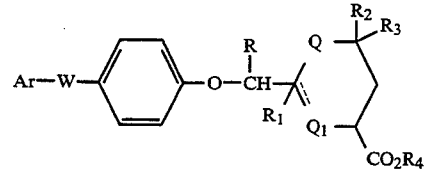

wherein Ar is

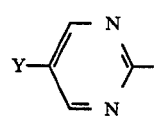

$Y$ is hydrogen, halogen, nitro, cyano or $C_1-C_4$ haloalkyl;
$W$ is O or S;
$R$ is $C_1-C_4$ alkyl;
$\rightleftharpoons$ indicates a single or double bond;
$R_1$ and $R_2$ are each independently hydrogen or $C_1-C_4$ alkyl, with the proviso that when $\rightleftharpoons$ indicates a double bond, then $R_1$ is not present;
$R_3$ is hydrogen, $C_1-C_4$ alkyl or $CO_2R_5$;
$Q$ is $S(O)_m$ and $Q_1$ is $NR_6$, with the proviso that when $\rightleftharpoons$ indicates a double bond then $R_6$ is not present;
$m$ is an integer of 0, 1 or 2;
$R_6$ is hydrogen or $C_1-C_4$ alkyl;
$R_4$ and $R_5$ are each independently hydrogen, $C_1$-$C_4$ alkyl optionally substituted with halogen, $C_1$-$C_4$ alkoxy, furyl, phenyl, halophenyl, $C_1$-$C_4$ alkylphenyl or $C_1$-$C_4$ alkoxyphenyl, $C_3$-$C_6$ alkenyl optionally substituted with $C_1$-$C_4$ alkoxy, halogen or phenyl, $C_3$-$C_6$ alkynyl optionally substituted with halogen, or an alkali metal, alkaline earth metal, manganese, copper, zinc, cobalt, silver, nickel, ammonium or organic ammonium cation;

the acid addition salts thereof when $R_6$ is hydrogen; or optical isomers or diastereomers thereof.

5. The method according to claim 4 wherein the herbicidally effective amount of the compound is applied in the presence of crops.

6. The method according to claim 5 wherein the undesirable vegetation is blackgrass, barnyardgrass, green foxtail, wild oats, large crabgrass and ryegrass and the crops are wheat, barley, soybean or rice.

7. The method according to claim 5 wherein the compound is applied to the crops and undesirable vegetation or to the soil or water containing seeds or other propagating organs of the undesirable vegetation, at the rate of about 0.016 kg/ha to 1.0 kg/ha.

8. A herbicidal composition comprising an inert carrier and an effective amount of a compound as described in claim 1.

* * * * *